United States Patent
Hudson

Patent Number: 5,456,711
Date of Patent: Oct. 10, 1995

[54] WARP KNITTED CAROTID PATCH HAVING FINISHED SELVEDGED EDGES

[75] Inventor: John O. Hudson, Clearwater, Fla.

[73] Assignee: Intervascular Inc., Clearwater, Fla.

[21] Appl. No.: 96,217

[22] Filed: Jul. 22, 1993

Related U.S. Application Data

[63] Continuation of Ser. No. 883,372, May 15, 1992, abandoned.

[51] Int. Cl.⁶ ........................................................ A61F 2/06
[52] U.S. Cl. ................... 623/1; 66/192; 66/195; 600/37; 602/44; 602/43; 602/76
[58] Field of Search .................. 602/42, 43, 44, 602/75, 76; 606/151, 152, 153, 155; 600/37; 623/1; 66/192, 195, 202

[56] References Cited

U.S. PATENT DOCUMENTS

| | | | |
|---|---|---|---|
| 3,570,013 | 3/1971 | Blumen | 623/1 |
| 3,922,888 | 12/1975 | Patterson | 66/195 |
| 3,945,052 | 3/1976 | Liebig | 128/334 |
| 4,193,137 | 3/1980 | Heck | 66/194 |
| 4,452,245 | 6/1984 | Usher | 606/151 |
| 4,540,398 | 9/1985 | Barson et al. | 66/195 |
| 4,856,299 | 8/1989 | Bryant | 66/195 |
| 5,053,021 | 10/1991 | Feibus | 66/195 |
| 5,100,422 | 3/1992 | Berguer et al. | 623/1 |

*Primary Examiner*—Paul Prebilic
*Attorney, Agent, or Firm*—Lerner, David, Littenberg, Krumholz & Mentlik

[57] ABSTRACT

A warp knitted vascular patch material, made in specific widths, the selvedges of the material are specially finished on the knitting machine without the introduction of additional threads to give a strong edge which will not fray and give firm support for the sutures. The specially knitted edges enables small neat sutures to be made without the risk of pulling out. This prevents all the problems of fraying edges and bulky seams found when unsized material is cut to the required width. This patch material is designed specifically for arterial closure following a carotid endorectomy.

18 Claims, 4 Drawing Sheets

5,456,711

WARP KNITTED CAROTID PATCH HAVING FINISHED SELVEDGED EDGES

This is a continuation of application Ser. No. 07/883,372, filed May 15, 1992 now abandoned.

FIELD OF THE INVENTION

This invention is directed to a warp knitted fabric patch, manufactured to specific widths and designed for closing the carotid artery after an endarectomy. The use of the patch prevents a reduction in size of the carotid artery due to sutures, and reduces the rate of restenosis.

BACKGROUND OF THE INVENTION

The partial blockage of the carotid artery by a build up of plaque, causes a reduction in the blood flow to the brain. The operation to clean out the deposits from the carotid artery is known as carotid endarectomy. After the artery is cut and the plaque removed, the artery must be resealed or "closed". The majority of carotid endarectomies performed today are done by primary closure. That is, the cut edges of the artery are simply sewn together. This procedure reduces the diameter of the artery and this can promote the possibility of restenosis. Several studies have shown that the risk of carotid restenosis after an endarectomy is reduced by patch closure. This is especially true of females who have smaller arteries than males.

Prior to the present invention there have been basic polyester fabric and PTFE patches. These however, have required cutting the patch to size at the operation site, and are prone to problems such as fraying, bleeding, suture line bleeding, suture pull-out and false aneurysms. All of these problems could result in an increased complication rate.

Another accessible material is the saphenous vein from the patient. A segment can be taken from the ankle or thigh area. In fact since a vein has a similar immune response to an artery, it has less chance of infection than a foreign body. However, vein patches can rupture, dilate and form aneurysms. Also since they have to be taken out, the operation becomes more complex and the removal site can cause more problems to the patient than the endarectomy.

As can be seen, it would be desirable to provide a special patch designed to be used specifically to close the carotid artery after a carotid endarectomy, without any of the problems found with the other prior methods.

SUMMARY OF THE INVENTION

The primary object of the invention is to provide a warp knitted carotid patch of a specific width, with finished selvedged edges to avoid the need to cut to width. This means that there are no fraying problems at the cut edge, and sutures may be made right at the extreme edge of the prosthesis. Cutting a narrow strip from a large piece is very difficult to perform, and leaves small particles of residue. Also, sutures cannot be made close to a cut edge or they will pull out. Suturing a cut edge therefore produces a very bulky irregular joint. Suturing a salvaged edge produces a very small even joint.

A carotid patch of the present invention is preferably made of 70 denier type 56 Dacron® polyester in reverse locknit warp knit construction. However, other structures are also possible including sharkskin construction and Queens cord construction.

BRIEF DESCRIPTION OF THE DRAWINGS

For a more detailed understanding of the invention and for illustration of various forms thereof, reference is to be made to the accompanying drawings, in which.

DESCRIPTION OF THE PREFERRED EMBODIMENTS

The carotid patches forming the subject matter of the present invention are manufactured by warp knitting a narrow strip of fabric at a particular width. The preferred construction is reverse locknit such as the carotid patch 10 shown in FIG. 1 but other constructions are also possible as hereinafter pointed out. Suitable yarns are polyester multifilament, between 40 and 100 denier. A preferred construction is reverse locknit, made from 70 denier 34 filament type 56 Dacron polyester, knitted on a Tricot type or Raschel type warp knitting machine with 28–32 needles per inch. Knitting machines of this type are well known in the knitting art.

The settings on the knitting machine, and the relative rates of yarn feed between the two sets of yarn used, are arranged to give a particular surface texture in one side of the fabric. This surface texture is in the form of raised loops of fiber on the technical face of the fabric and is commonly referred to as a velour surface. This velour surface is used on the outside of the carotid patch, with the smooth side forming the lumen of the carotid artery.

Figure 1:
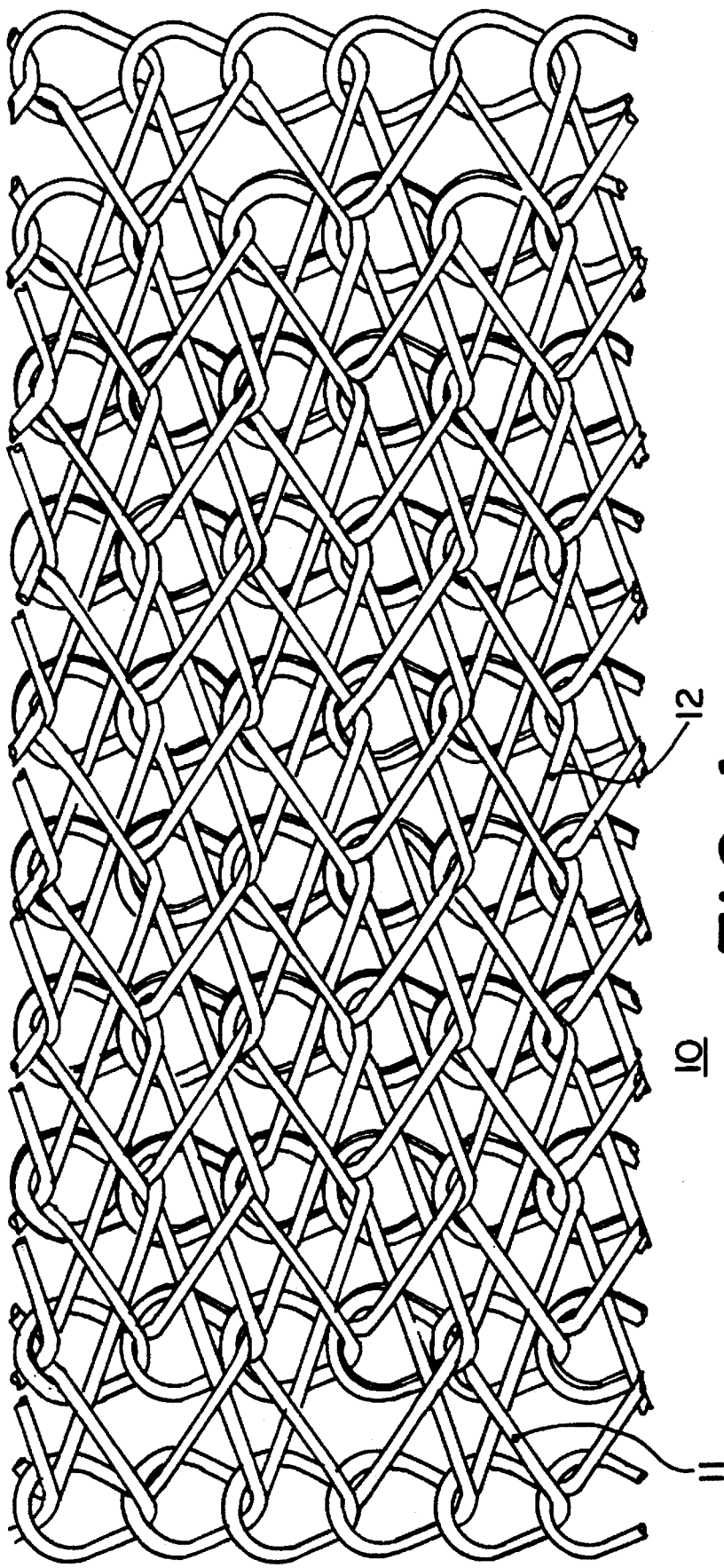
FIG. 1 diagrammatically illustrates a warp knitted carotid patch made according to the present invention having a reverse locknit construction.
Figure 2:
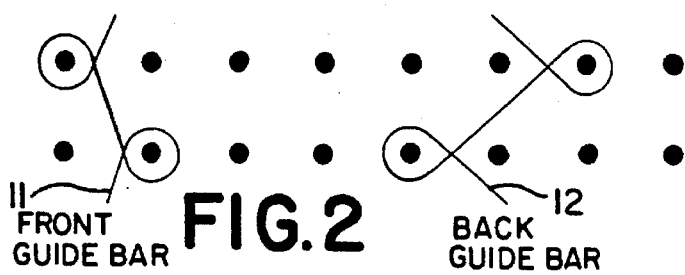
FIG. 2 is the point paper diagram of the reverse locknit structure of FIG. 1 including the front guide bar and back guide bar.
Figure 3:
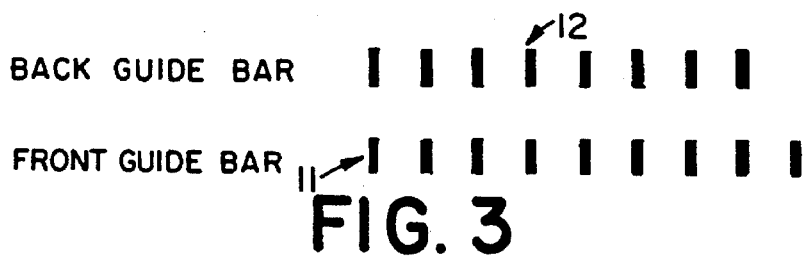
FIG. 3 diagrammatically illustrates the correct threading and gaiting at the warp knitting machine start for a ten needle wide reverse locknit construction as shown in FIG. 1.

Referring to FIG. 1 there is shown the construction of the carotid fabric patch 10 made according to the present invention using ten needles. FIG. 2 shows the point paper notation for the fabric in FIG. 1. The front guide bar is threaded with nine threads, (shown as 11 on FIG. 1) and the back guide bar is threaded with eight threads shown (shown as 12 on FIG. 1). By arranging the relative positions of the front and back bar threads 11 and 12 correctly, a finished edge or salvage is formed. This correct relative position or gaiting is very important since incorrect gaiting will form a ragged edge. The correct threading and gaiting at the machine start is shown in FIG. 3 for reverse locknit. Any width of patch may be made, so long as the number of ends of yarn on the front bar is one less than the number of needles, and the number of ends in the back bar is two less than the number of needles, and the gaiting is correct.

Figure 5:
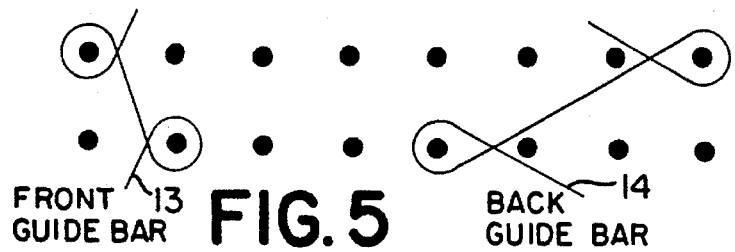
FIG. 5 is a point paper diagram of the sharkskin construction shown in FIG. 4 including the front guide bar and the back guide bar.
Figure 6:
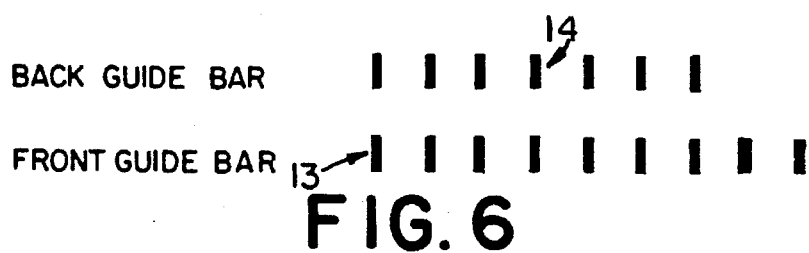
FIG. 6 diagrammatically illustrates the correct threading and gaiting for a ten needle wide carotid patch of sharkskin construction as shown in FIG. 4.
Figure 8:
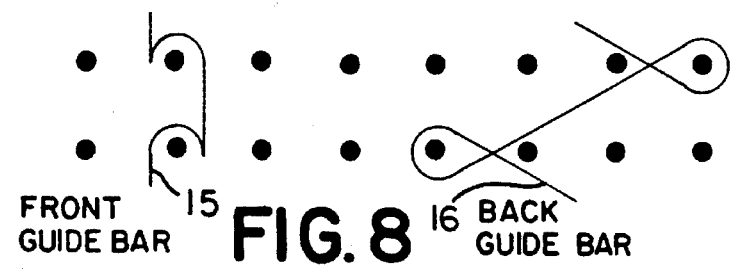
FIG. 8 is a point paper diagram of the Queens cord construction shown in FIG. 7 including the front guide bar and the back guide bar.
Figure 9:
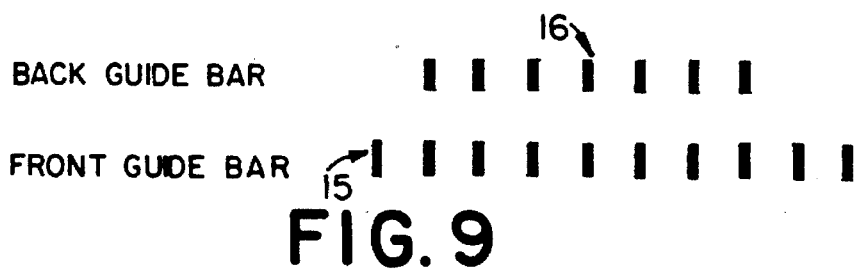
FIG. 9 diagrammatically illustrates the correct threading and gaiting for a ten needle wide carotid patch of Queens cord construction as shown in FIG. 7.
Figure 4:
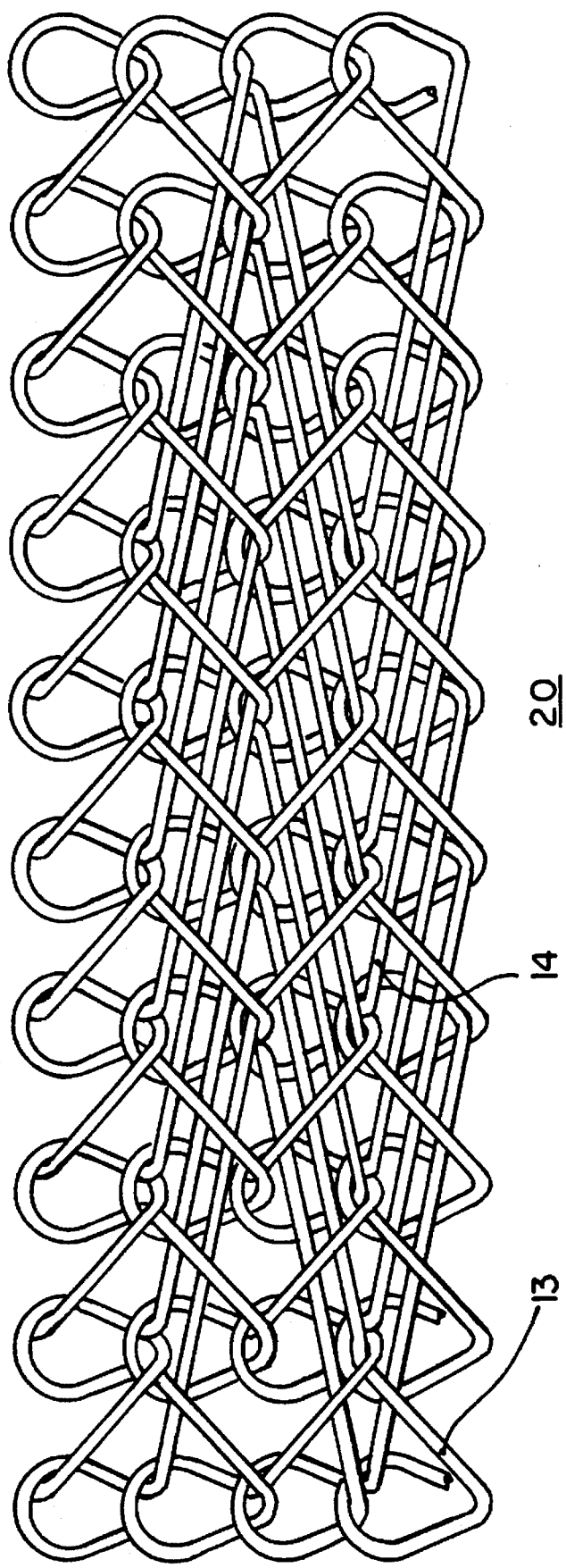
FIG. 4 diagrammatically illustrates a warp knitted carotid patch according to the present invention having a sharkskin construction.
Figure 7:
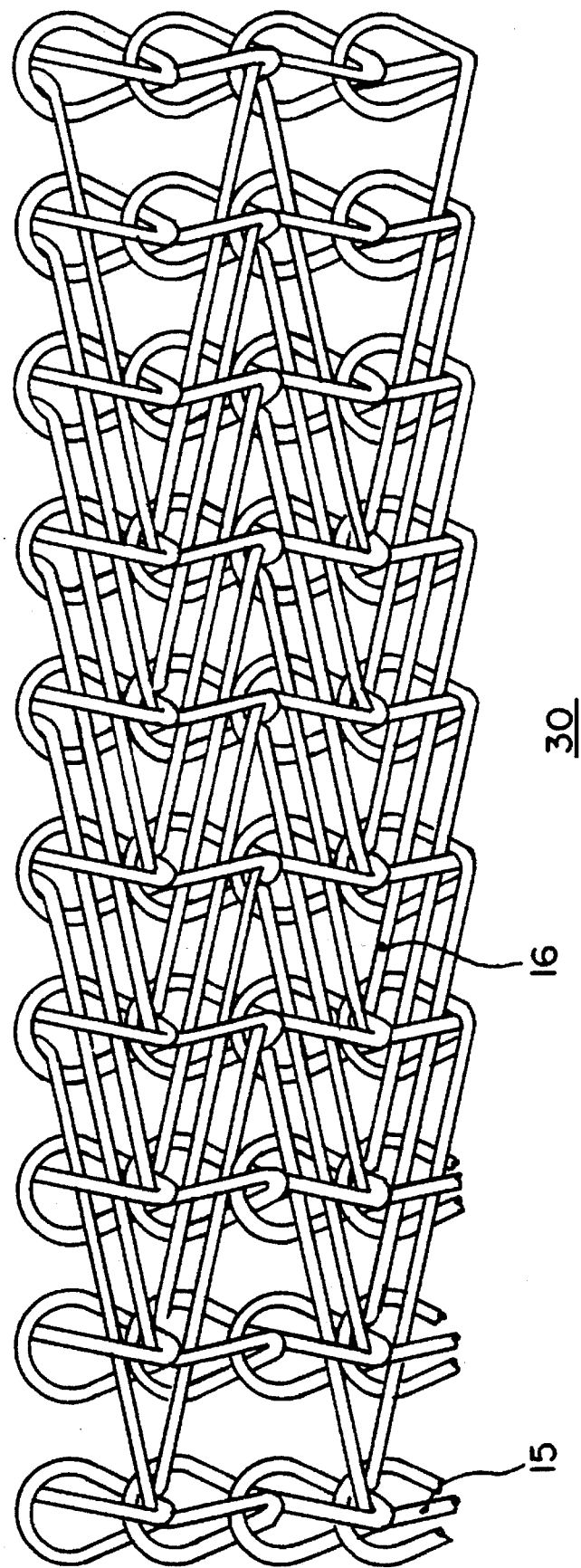
FIG. 7 diagrammatically illustrates a warp knitted carotid patch embodying the present invention having a Queens cord construction.

Other fabric constructions for the patch are also suitable for this invention, including, sharkskin as shown by the patch 20 in FIG. 4 and Queens cord as shown by the patch 30 in FIG. 7. FIG. 5 shows the point paper notations of sharkskin, and FIG. 6 shows the correct threading and gaiting for a ten needle wide patch of sharkskin having nine threads 13 in the front guide bar and seven threads, 14 in the back bar. FIG. 8 shows the point paper notation for Queens cord and FIG. 9 shows the correct threading and gaiting for a ten needle wide patch of Queens cord having ten threads 15 in the front guide bar and seven threads 16 in the back guide bar.

After knitting, the continuous strips of patch fabric are washed and heat treated to allow full relaxation or compaction, and then pressed flat. After pressing, they are cut to the required length and packaged.

A range of widths is required to meet all needs and the different widths are knitted on the warp knitting machine to give finished knitted selvedge. A complete range of widths may be made without the need for cutting. Thus the edges are completely free from fraying, and sutures may be placed at the very edge of the patch. A preferred range of widths is from 4 mm wide to 16 mm wide. When using the preferred construction of 70 denier yarn on a thirty needle per inch knitting machine, ten needles as in FIG. 1 would yield a patch 5 mm wide. However, the actual finished width depends on both the knitting set-up and the finishing technique. These techniques can be varied if, for example, a different porosity is required. The porosity normally is chosen to be fairly high which makes for good healing. The high porosity (about 1800 ml/cm$^2$/min/120 Hg) is not a problem since the prosthesis is so small that it is easy to pre-clot. In use the smooth side is placed inside the artery and the outer texturous surface allows good tissue ingrowth.

While there has been described a preferred embodiment of the invention, it will be understood that further modifications may be made without departing from the spirit and scope of the invention as set forth in the appended claims.

What is claimed is:

1. A warp knitted carotid patch for arterial closure after an endarectomy, said carotid patch comprising a warp knitted yarn having a predetermined width dimensioned for closure of said artery after said endarectomy and with finished knitted selvedged edges consisting essentially of said warp knitted yarn to avoid the need to cut to width.

2. A warp knitted carotid patch according to claim 1 wherein said carotid patch is fabricated on a knitting machine having front and rear guide bars threaded and gaited to produce said finished knitted selvedged edges.

3. A warp knitted carotid patch according to claim 1 having a reverse locknit structure.

4. A warp knitted carotid patch according to claim 1 wherein said warp knitted yarn comprises a polyester yarn.

5. A warp knitted carotid patch according to claim 3 wherein said polyester yarn comprises 56 gauge polyester.

6. A warp knitted carotid patch according to claim 1 wherein said yarn count is in the range of 40 denier to 100 denier.

7. A warp knitted carotid patch according to claim 6 wherein said polyester yarn comprises 70 denier 34 filament.

8. A warp knitted carotid patch according to claim 1 wherein one surface of said patch comprises filaments of yarn raised in loops above the surface to form a raised texture or velour.

9. A warp knitted carotid patch according to claim 1 wherein said warp knitting machine has a gauge range of between 28 and 32 needles per inch.

10. A warp knitted carotid patch according to claim 1 having a sharkskin construction.

11. A warp knitted carotid patch according to claim 1 having a queen's cord construction.

12. A warp knitted carotid patch according to claim 1 having a width within the range of from about 4 mm to about 16 mm wide.

13. A warp knitted carotid patch for arterial closure after an endarectomy, said carotid patch having a first surface and a second surface, said first surface being substantially smooth, and said second surface being characterized by filaments of yarn raised in loops above said second surface to form a raised texture or velour, said carotid patch further having a predetermined width dimensioned for closure of said artery after said endarectomy and with finished knitted selvedged edges to avoid the need to cut to width.

14. A warp knitted carotid patch according to claim 13 wherein said carotid patch is fabricated on a knitting machine having front and rear guide bars threaded and gaited to produce said finished selvedged edges.

15. A warp knitted carotid patch according to claim 13 having a reverse locknit construction.

16. A warp knitted carotid patch according to claim 13 having a sharkskin construction.

17. A warp knitted carotid patch according to claim 13 having a queen's cord construction.

18. A warp knitted carotid patch according to claim 13 wherein said warp knitted yarn comprises polyester.

* * * * *

UNITED STATES PATENT AND TRADEMARK OFFICE
CERTIFICATE OF CORRECTION

PATENT NO. : 5,456,711
DATED : October 10, 1995
INVENTOR(S) : John O. Hudson

It is certified that error appears in the above-identified patent and that said Letters Patent is hereby corrected as shown below:

Column 4, line 14 "6" should read --4--.

Signed and Sealed this

Sixteenth Day of January, 1996

Attest:

BRUCE LEHMAN

Attesting Officer

Commissioner of Patents and Trademarks